United States Patent
Jung et al.

(10) Patent No.: US 8,835,870 B2
(45) Date of Patent: Sep. 16, 2014

(54) TARGETS FOR GENERATING IONS AND TREATMENT APPARATUSES USING THE TARGETS

(71) Applicant: Electronics and Telecommunications Research Institute, Daejeon (KR)

(72) Inventors: Moon Youn Jung, Daejeon (KR); Hyeon-Bong Pyo, Daejeon (KR); Hyung Ju Park, Suwon (KR); Seunghwan Kim, Daejeon (KR); Seon Hee Park, Daejeon (KR); Dong-Ho Shin, Daejeon (KR); Hwang Woon Lee, Suwon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

(21) Appl. No.: 13/737,706

(22) Filed: Jan. 9, 2013

(65) Prior Publication Data

US 2013/0178689 A1    Jul. 11, 2013

(30) Foreign Application Priority Data

Jan. 9, 2012  (KR) .................. 10-2012-0002588
Sep. 17, 2012 (KR) .................. 10-2012-0103021

(51) Int. Cl.
 *G21K 5/04*    (2006.01)
(52) U.S. Cl.
 USPC ............... 250/423 P; 250/423 R; 250/424; 315/111.01; 315/111.81; 315/111.91

(58) Field of Classification Search
 USPC ............. 250/423 R, 424, 423 P; 315/111.01, 315/111.81, 111.91
 See application file for complete search history.

(56) References Cited

U.S. PATENT DOCUMENTS

| | | | |
|---|---|---|---|
| 2012/0298624 A1* | 11/2012 | Cowan et al. .................... | 216/41 |
| 2013/0068956 A1* | 3/2013 | Friedman ....................... | 250/382 |
| 2013/0153783 A1* | 6/2013 | Zigler et al. ................ | 250/423 P |

OTHER PUBLICATIONS

In-Yong Park et al., "Plasmonic generation of ultrashort extreme-ultraviolet light pulses", Nature Photonics, Nov. 2011, pp. 677-681, vol. 5, Macmillan Publishers Limited.

* cited by examiner

*Primary Examiner* — Nicole Ippolito (57) ABSTRACT

Provided is an ion beam treatment apparatus including the target. The ion beam treatment apparatus includes a substrate having a first surface and a second surface opposed to the first surface, and including a cone type hole decreasing in width from the first surface to the second surface to pass through the substrate, wherein an inner wall of the substrate defining the cone type hole is formed of a metal, an ion generation thin film attached to the second surface to generate ions by a laser beam incident into the cone type hole through the first surface and strengthen, and a laser that emits a laser beam to generate ions from the ion generation thin film and project the ions onto a tumor portion of a patient. The laser beam incident into the cone type hole is focused by the cone type hole and is strengthened.

20 Claims, 5 Drawing Sheets

TARGETS FOR GENERATING IONS AND TREATMENT APPARATUSES USING THE TARGETS

CROSS-REFERENCE TO RELATED APPLICATIONS

This U.S. non-provisional patent application claims priority under 35 U.S.C. §119 of Korean Patent Application Nos. 10-2012-0002588, filed on Jan. 9, 2012, and 10-2012-0103021, filed on Sep. 17, 2012, the entire contents of which are hereby incorporated by reference.

BACKGROUND OF THE INVENTION

The present invention disclosed herein relates to a target for generating ions and a treatment apparatus using the target, and more particularly, to a target for generating protons or carbon ions and an ion beam treatment apparatus using the target.

Methods for radiotherapy may include X-ray treatments, electron beam treatments, and ion beam treatments. Of these, the X-ray treatments are the lowest-cost treatment methods using the simplest device and are thus being most commonly used at the present day. Although it has been proven in 1950's that tumors can be treated by accelerating electrons using an accelerator to inject the electrons into the tumors, the electron beam treatments had not been taken over as one method for radiotherapy until electron accelerators were miniaturized in 1980's. In the X-ray treatments or the electron beam treatments, hydrogen bonds within cancer cells can be cut to destroy DNAs of the cancer cells. However, side effects in which healthy cells existing within the traveling path of X-rays or electron beams are seriously damaged may occur. Technologies such as intensity-modulated radiation therapy (IMRT), tomo therapy, and cyber knife have been developed as methods for reducing the radiation exposure of normal cells. However, the technologies cannot completely solve the above-described side effects.

The ion beam treatments are in the spotlight as treatment methods which can mitigate the side effects due to the X-ray treatments or the electron beam treatments. To allow the ion beam to penetrate a material, the ion beam should be accelerated to have high velocity, like the electrons. Even though the ion beam is gradually decreased in velocity when the ion beam penetrates a certain material, the ion beam is subject to the most energy loss of ionizing radiation just before the ion beam is stopped. This phenomenon is called a Bragg peak after William Henry Bragg, which discovered the phenomenon in 1903. Thus, in a case of such an ion beam treatment, malignant tumors may be selectively and locally treated when the ions are precisely controlled in velocity. When tumors are disposed at a deep position of the human body, protons or ions should be accelerated to a significantly high energy level at the outside of the human body. Methods of accelerating protons or ions may include a laser driven ion acceleration method. When high-power laser beam is emitted to a thin film, ions or protons within the thin film may escape with acceleration energy by a target normal sheath acceleration model (TNSA model) or a radiation pressure acceleration model (RPA model). After that, the ions may penetrate the body of a patient according to the acceleration energy to stop at a predetermined depth corresponding to the location of a tumor, and a large amount of free oxygen radicals may be generated at the predetermined depth to necrotize the tumor cells, which is a general principle of the ion beam treatment.

Ions, used in the ion beam treatment using the laser driven ion acceleration method, have the following two properties. First, the ions should have high energy to arrive at a deep portion of a human body. Secondly, most of the ions should have substantially the same energy. Protons, having an energy level of about 250 MeV, can arrive at a portion located at a depth of about 20 cm in a human body. For example, ions having a high energy level of about 70 MeV may be used in a retinoblastoma treatment, and ions having a high energy level of about 200 MeV or higher may be used to treat a caner in a deep portion of a human body.

In addition, most of the protons or ions generated using a femtosecond laser should have uniform energy. Otherwise, ions may not be collected only in a tumor region. Accordingly, a normal tissue located out of the tumor region may be exposed to radiation.

In order to satisfy the two properties of ions, a target as an ion source should have a significantly small thickness. Thus, the target should be an ultra thin film.

In addition, a laser for accelerating the ions should have a significantly high energy of about $10^{19}$ to $10^{21}$ W/cm². This requires a significantly large laser system and high costs.

SUMMARY OF THE INVENTION

The present invention provides an ion generation target for generating protons or carbon ions of high energy, and an ion beam treatment apparatus using the ion generation target.

Embodiments of the present invention provide ion generation targets including: a substrate having a first surface and a second surface opposed to the first surface, and including a cone type hole decreasing in width from the first surface to the second surface to pass through the substrate; a cone type metal thin film disposed on an inner surface of the substrate exposed by the cone type hole; and an ion generation thin film attached to the second surface of the substrate to generate ions by means of a laser beam incident to the inside of the cone type metal thin film through the first surface of the substrate and strengthen.

In some embodiments, the cone type metal thin film may include silver, copper, gold, or aluminum.

In other embodiments, an inner circumferential surface of the cone type metal thin film may be treated by mirror-like finishing.

In still other embodiments, the ion generation targets may further include inert gas in the cone type metal thin film.

In even other embodiments, the substrate may include an insulating material.

In yet other embodiments, the ion generation targets may further include inert gas inside of the cone type metal thin film.

In further embodiments, the cone type metal thin film may have an inner diameter of about tens μm in the first surface of the substrate, and an inner diameter ranging from about tens nm to about several μm in the second surface of the substrate.

In still further embodiments, the ions may be protons or carbon ions.

In even further embodiments, the ions may be protons, and the ion generation thin film may be formed of a material containing hydrogen.

In yet further embodiments, the material containing hydrogen may be a silicon nitride, a silicon oxide, or a metal.

In much further embodiments, the ions may be carbon ions, and the ion generation thin film may include graphene, fullerenes in which carbon atoms are connected to one another in a spherical shape or a column shape, or carbon nanotube.

In other further embodiments, the substrate may include cone type holes that are distributed in a predetermined arrangement.

In other embodiments of the present invention, ion generation targets include: a metal substrate having a first surface and a second surface opposed to the first surface, and including a cone type hole decreasing in width from the first surface to the second surface to pass through the substrate; and an ion generation thin film attached to the second surface of the substrate to generate ions by means of a laser beam incident into the cone type hole through the first surface of the substrate and strengthen.

In some embodiments, a surface of the metal substrate exposed by the cone type hole may be treated by mirror-like finishing.

In other embodiments, the metal substrate may include silver, copper, gold, or aluminum.

In still other embodiments, the ion generation targets may further include inert gas in the cone type hole.

In even other embodiments, the cone type hole may have a diameter of about tens μm in the first surface of the substrate, and a diameter ranging from about tens nm to about several μm in the second surface of the substrate.

In yet other embodiments, the ions may be protons or carbon ions.

In further embodiments, the ions may be protons, and the ion generation thin film may be formed of a material containing hydrogen.

In still further embodiments, the material containing hydrogen may be a silicon nitride, a silicon oxide, or a metal.

In even further embodiments, the ions may be carbon ions, and the ion generation thin film may include graphene, fullerenes in which carbon atoms are connected to one another in a spherical shape or a column shape, or carbon nanotube.

In yet further embodiments, the metal substrate may include cone type holes that are distributed in a predetermined arrangement.

In even other embodiments of the present invention, ion beam treatment apparatuses include: the above-described ion generation target; and a laser that emits a laser beam into the cone type hole through the first surface of the substrate to generate ions from the ion generation thin film and project the ions onto a tumor portion of a patient, wherein the laser beam incident into the cone type hole is focused by the cone type hole and is strengthened, and the ions are emitted from the ion generation thin film by the strengthened laser beam.

In some embodiments, the inner wall of the substrate exposed through the cone type hole may be treated by mirror-like finishing.

In other embodiments, the ion beam treatment apparatuses may further include inert gas in the cone type hole.

In still other embodiments, the laser may be disposed at a side of the first surface of the substrate.

In even other embodiments, the laser beam may be a femtosecond laser beam.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Embodiments of the present invention will be described below in detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Like reference numerals refer to like elements throughout.

In the following description, the technical terms are used only for explaining specific exemplary embodiments while not limiting the present invention. The terms of a singular form may include plural forms unless referred to the contrary. The meaning of 'comprises' and/or 'comprising' specifies a property, a region, a fixed number, a step, a process, an element and/or a component but does not exclude other properties, regions, fixed numbers, steps, processes, elements and/or components. Since exemplary embodiments are provided below, the order of the reference numerals given in the description is not limited thereto. In the specification, it will be understood that when a layer (or film) is referred to as being 'on' another layer or substrate, it can be directly on the other layer or substrate, or intervening layers may also be present.

Additionally, the embodiments in the detailed description may be described with cross-sectional views and/or plan views as ideal exemplary views of the present invention. In the figures, the dimensions of layers and regions are exaggerated for clarity of illustration. Accordingly, shapes of the exemplary views may be modified according to manufacturing techniques and/or allowable tolerances. Therefore, the embodiments of the present invention are not limited to the specific shape illustrated in the exemplary views, but may include other shapes that may be created according to manufacturing processes. For example, an etched region illustrated as a rectangle may have rounded or curved features. Thus, areas exemplified in the drawings have general properties, and are used to illustrate a specific shape of a device region. Accordingly, this should not be construed as limited to the scope of the present invention.

Figure 1:
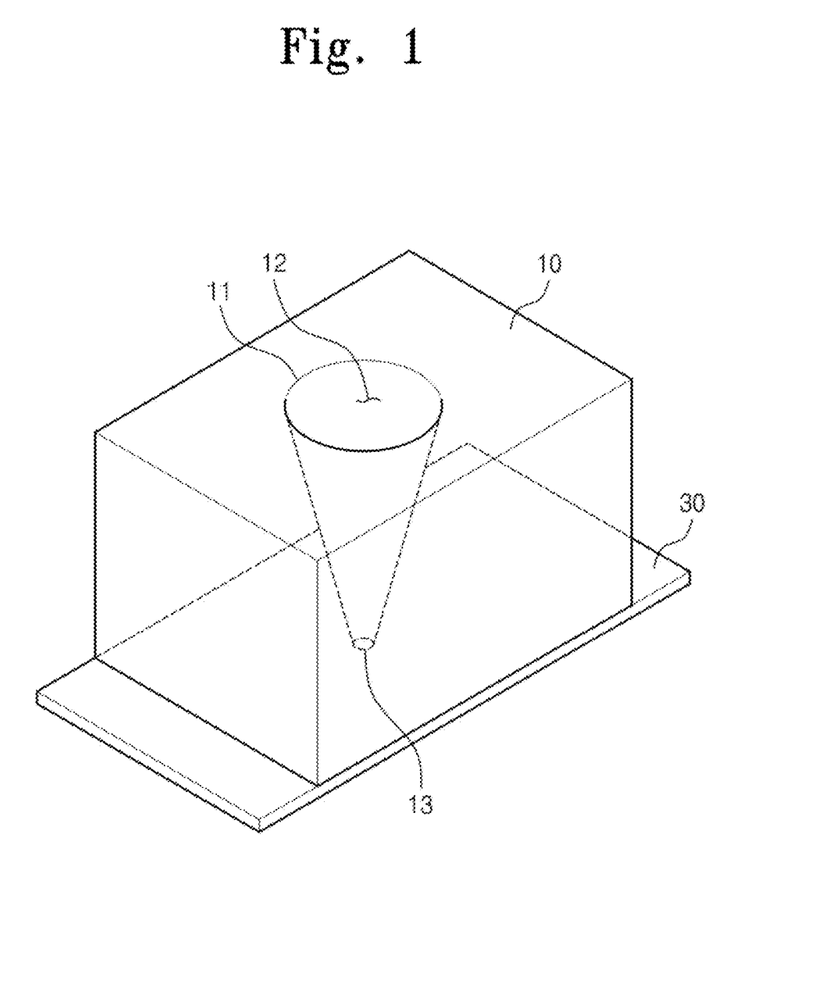
FIG. 1 is a perspective view illustrating an ion generation target used in an ion beam treatment apparatus according to an embodiment of the present invention.

FIG. 1 is a perspective view illustrating an ion generation target used in an ion beam treatment apparatus according to an embodiment of the present invention.

Referring to FIG. 1, an ion generation target includes a substrate 10 including a cone type hole 12, and an ion generation thin film 30 attached to a surface of the substrate 10.

The substrate 10 may have a first surface and a second surface opposed to the first surface. The cone type hole 12 may decrease in width from the first surface to the second surface to pass through the substrate 10. That is, the cone type hole 12 may have a tapered structure in which a diameter thereof in the first surface is greater than a diameter in the second surface. The cone type hole 12 may have a diameter of about tens μm in the first surface of the substrate 10, and a diameter ranging from about tens nm to about several μm in the second surface of the substrate 10. An end of the cone type hole 12 in the first surface of the substrate 10 is an incidence hole 11 through which a laser beam (see 20 of FIG. 2) is incident, and the other end of the cone type hole 12 in the second surface of the substrate 10 is an emission hole 13 through which the laser beam is emitted.

The substrate 10 may include a metal material having significantly high electric conductivity. The metal material may include silver (Ag), copper (Cu), gold (Au), or aluminum (Al). A surface of the substrate 10, exposed by the cone type hole 12, may be treated by mirror-like finishing. This is because the cone type hole 12 focuses an incident laser beam to increase the energy of the laser beam, i.e., the intensity thereof, and because as reflectivity of the cone type hole 12 for a laser beam is increased, the intensity of the laser beam is increased. In addition, since the cone type hole 12 has a tapered structure, the cone type hole 12 can focus a laser beam, like a convex lens does. That is, the cone type hole 12 has the same function as that of a laser cavity. As such, a laser beam is focused by the cone type hole 12 that decreases in width in a propagation direction of the laser beam. Accordingly, the intensity of the laser beam is increased.

The substrate 10 may include an insulating material. The insulating material may include glass, silicon, or polymer. When the substrate 10 includes an insulating material, a cone type metal thin film (see 15 of FIG. 2) may be disposed on an inner surface of the substrate 10 exposed by the cone type hole 12. The cone type metal thin film may include one of silver, copper, gold, and aluminum, which are metals having high electric conductivity. The cone type metal thin film may have an inner diameter of about tens μm in the first surface of the substrate 10, and an inner diameter ranging from about tens nm to about several μm in the second surface of the substrate 10. The inner circumferential surface of the cone type metal thin film may be treated by mirror-like finishing. Accordingly, the cone type metal thin film may have the same effect as that of the cone type hole 12. That is, the cone type metal thin film may have the same function as that of a laser cavity. Thus, a laser beam may be focused by the cone type metal thin film that decreases in width in a propagation direction of the laser beam. Accordingly, the intensity of the laser beam is increased.

The ion generation thin film 30 may be attached to the second surface of the substrate 10.

When the laser beam (see 20 of FIG. 3) is incident into the cone type hole 12, the intensity of the laser beam may be increased by the cone type hole 12 or the cone type metal thin film, to thereby generate ions (see 32 of FIG. 3) from the ion generation thin film 30. The ions may be protons or carbon ions.

When the ions are protons, the ion generation thin film 30 may be formed of a material containing hydrogen (H). The material containing hydrogen may be a silicon nitride, a silicon oxide, or a metal. When the ions are carbon ions, the ion generation thin film 30 may include graphene, fullerenes in which carbon atoms are connected to one another in a spherical shape or a column shape, or carbon nanotube.

Figure 2:
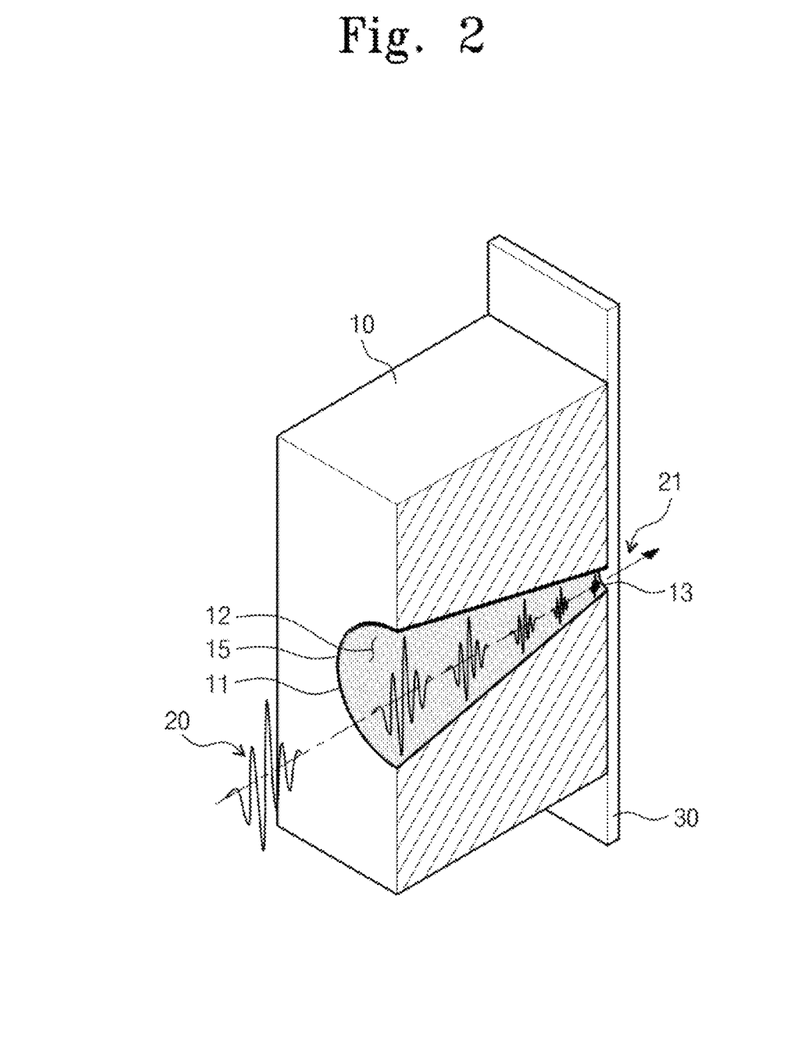
FIG. 2 is a cut-away perspective view illustrating phenomena occurring in an ion generation target used in an ion beam treatment apparatus according to an embodiment of the present invention.

FIG. 2 is a cut-away perspective view illustrating phenomena occurring in an ion generation target used in an ion beam treatment apparatus according to an embodiment of the present invention.

Referring to FIG. 2, when the laser beam 20 is incident into the incidence hole 11 of the cone type hole 12 of the substrate 10, the intensity of the laser beam 20 is increased by the cone type hole 12 functioning as a laser cavity. A strengthen laser beam 21, formed by increasing the intensity of the laser beam 20, may transfer energy to the ion generation thin film 30 attached to the portion of the substrate 10 including the emission hole 13. As described above, when the substrate 10 may include an insulating material, the cone type metal thin film 15 may be disposed on the inner surface of the substrate 10 exposed by the cone type hole 12. The transferred energy may generate the ions (see 32 of FIG. 3) from the ion generation thin film 30. At this point, the intensity of the strengthen laser beam 21 may be several times to hundreds of times greater than the intensity of the laser beam 20 incident into the incidence hole 11.

Figure 3:
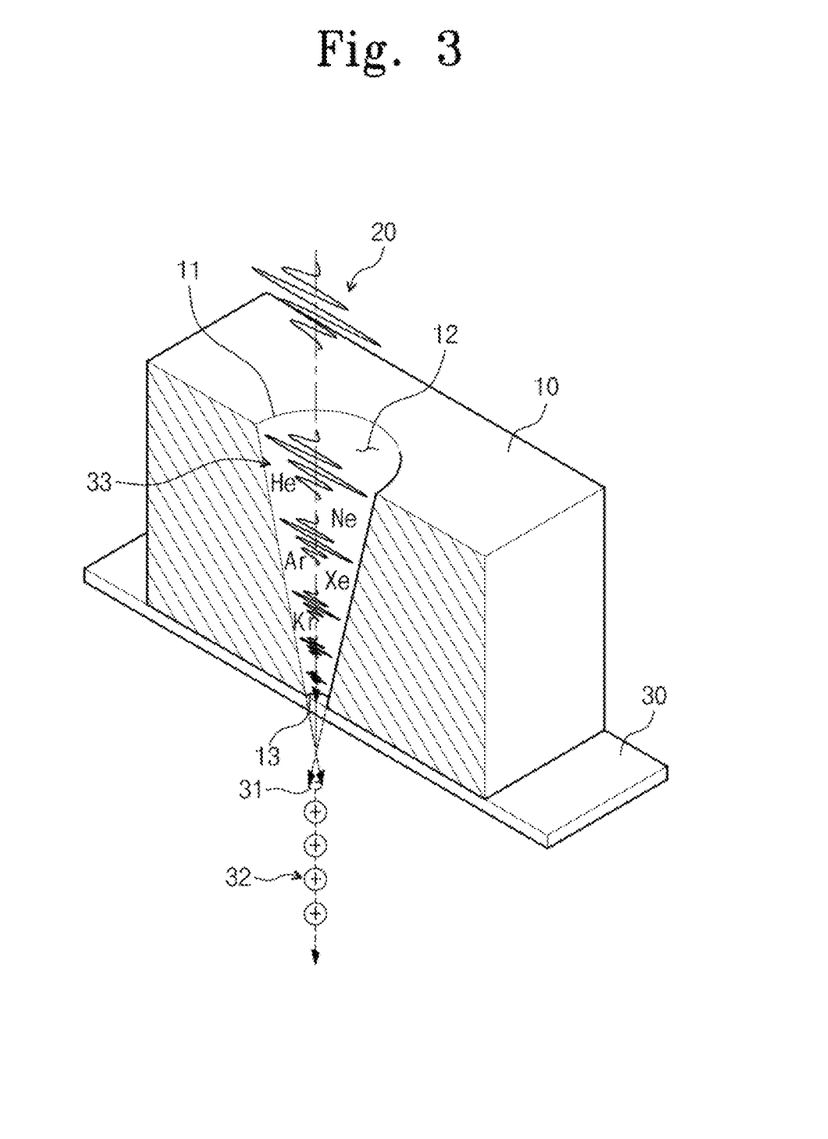
FIG. 3 is a cut-away perspective view illustrating another phenomena occurring in an ion generation target used in an ion beam treatment apparatus according to an embodiment of the present invention.

FIG. 3 is a cut-away perspective view illustrating another phenomena occurring in an ion generation target used in an ion beam treatment apparatus according to an embodiment of the present invention.

Referring to FIG. 3, the current embodiment is different from the embodiment of FIG. 2 in that inert gas 33 (He, Ne, Ar, Kr, or Xe etc.) may be accommodated in the cone type hole 12 of the substrate 10 under a predetermined pressure.

The inert gas 33 may be excited by the energy of the laser beam 20 incident into the cone type hole 12 to emit photons that generate a higher order harmonic wave 31 by a frequency doubling process. The higher order harmonic wave 31, as a strengthen laser beam, ionizes atoms contained in the ion generation thin film 30, thereby generating the ions 32 that are accelerated to a significantly high energy level by the higher order harmonic wave 31, so that the ions 32 can be projected onto a tumor portion (see 54 of FIG. 5) of a human body.

Figure 4A:
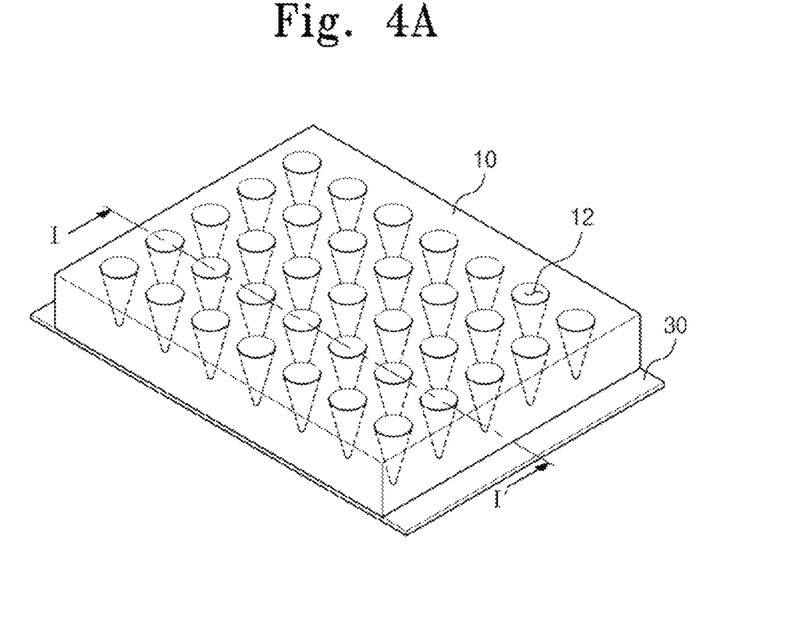
FIG. 4A is a perspective view illustrating an ion generation target used in an ion beam treatment apparatus according to another embodiment of the present invention.
Figure 4B:
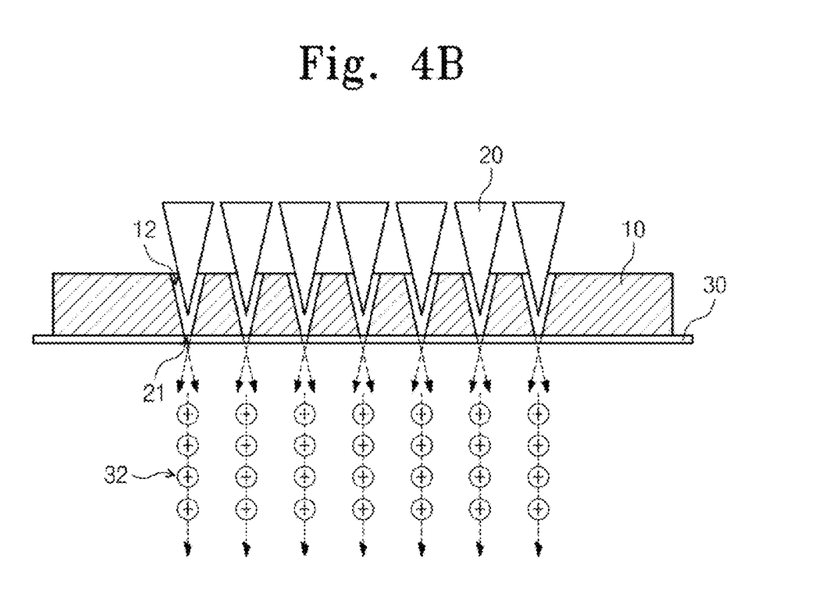
FIG. 4B is a cross-sectional view taken along line I-I' of FIG. 4A.

FIG. 4A is a perspective view illustrating an ion generation target used in an ion beam treatment apparatus according to another embodiment of the present invention. FIG. 4B is a cross-sectional view taken along line I-I' of FIG. 4A.

Referring to FIGS. 4A and 4B, a substrate 10 of an ion generation target may have a plurality of cone type holes 12. That is, the cone type holes 12 may be uniformly and entirely distributed in the substrate 10. The cone type holes 12 may be distributed in a predetermined arrangement, but the arrangement of the cone type holes 12 is not specifically limited.

When a laser beam 20 is incident into one of the cone type holes 12 and is focused, ions 32 may be accelerated at a point of an ion generation thin film 30. Then, another laser beam 20 may be incident into another cone type hole 12 and be focused, and ions 32 may be accelerated at another point of the ion generation thin film 30. In this manner, laser beams 20 may be sequentially incident into the cone type holes 12 and be focused, thereby continuously projecting ions 32 onto the tumor portion (see 54 of FIG. 5) of the human body. Alternatively, when the laser beams 20 are simultaneously incident into the cone type holes 12 and be focused, the ions 32 can be projected onto a tumor portion having a large area in the human body.

Figure 5:
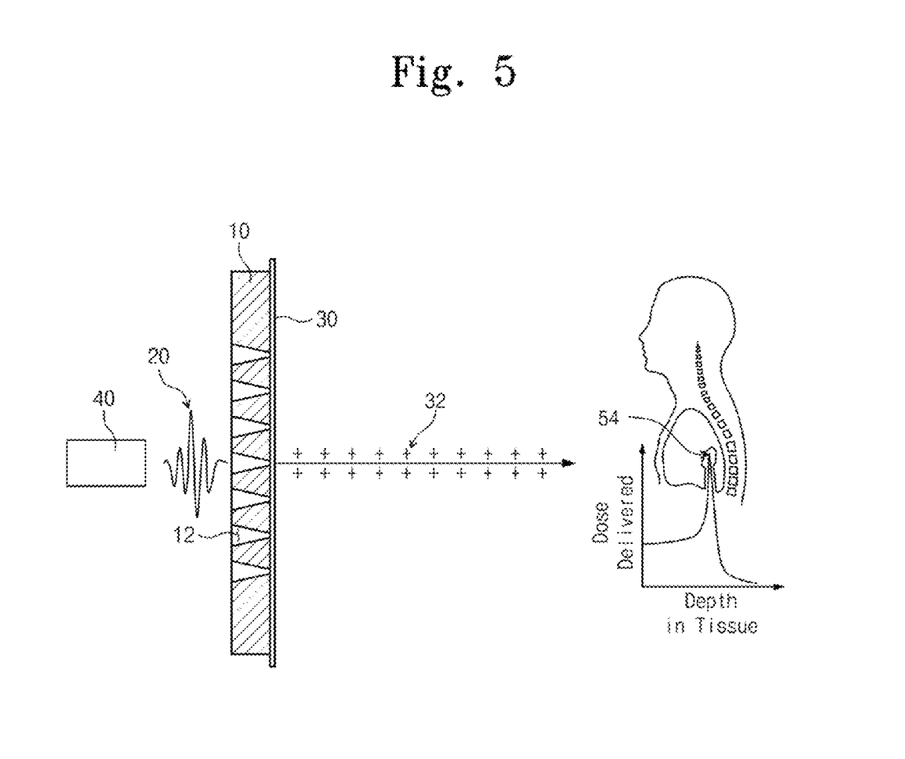
FIG. 5 is a schematic view illustrating an ion beam treatment apparatus according to an embodiment of the present invention.

FIG. 5 is a schematic view illustrating an ion beam treatment apparatus according to an embodiment of the present invention.

Referring to FIG. 5, an ion beam treatment apparatus includes a laser 40 and an ion generation target.

A laser 40 may generate ions 32 from an ion generation target and project the ions 32 onto a tumor portion 54 in a patient. The laser 40 may emit a laser beam 20 to the ion generation target. The laser 40 may be disposed at a side of a first surface of a substrate 10 opposite to an ion generation thin film 30 of the ion generation target. The laser beam 20 may be a femtosecond laser beam.

The ion generation target may generate the ions 32 be receiving the laser beam 20 from the laser 40. The ion generation target may include the substrate 10 having cone type holes 12, and the ion generation thin film 30 attached to a surface of the substrate 10.

The substrate 10 may have the first surface and a second surface opposite to the first surface. The cone type holes 12 may have a structure tapered with a predetermined angle from the first surface toward the second surface, to pass through the substrate 10. That is, the cone type hole 12 may have a tapered structure in which a diameter thereof in the first surface is greater than a diameter in the second surface. The cone type hole 12 may have a diameter of about tens um in the first surface of the substrate 10, and a diameter ranging from about tens nm to about several μm in the second surface of the substrate 10. An end of the cone type hole 12 in the first surface of the substrate 10 is an incidence hole (see 11 of FIG. 1) through which the laser beam 20 is incident, and the other end of the cone type hole 12 in the second surface of the substrate 10 is an emission hole (see 13 of FIG. 1) through which the laser beam 20 is emitted.

The substrate 10 may include a metal material having significantly high electric conductivity. The metal material may include silver, copper, gold, or aluminum. Surfaces of the substrate 10, exposed by the cone type holes 12, may be treated by mirror-like finishing. This is because the cone type holes 12 focus an incident laser beam to increase the energy of the laser beam, i.e., the intensity thereof, and because as reflectivity of the cone type holes 12 for a laser beam is increased, the intensity of the laser beam is increased. In addition, since the cone type hole 12 has a tapered structure, the cone type hole 12 can focus a laser beam, like a convex lens does. That is, the cone type hole 12 has the same function as that of a laser cavity. As such, a laser beam is focused by the cone type hole 12 that decreases in width in a propagation direction of the laser beam. Accordingly, the intensity of the laser beam is increased.

The substrate 10 may include an insulating material. The insulating material may include glass, silicon, or polymer. When the substrate 10 includes an insulating material, cone type metal thin films (see 15 of FIG. 2) may be disposed on inner surfaces of the substrate 10 exposed by the cone type holes 12. The cone type metal thin film may include one of silver, copper, gold, and aluminum, which are metals having high electric conductivity. The cone type metal thin film may have an inner diameter of about tens μm in the first surface of the substrate 10, and an inner diameter ranging from about tens nm to about several μm in the second surface of the substrate 10. The inner circumferential surfaces of the cone type metal thin films may be treated by mirror-like finishing. Accordingly, the cone type metal thin films 15 may have the same effect as that of the cone type hole 12. That is, the cone type metal thin film may have the same function as that of a laser cavity. Thus, the laser beam 20 may be focused by the cone type metal thin film that decreases in width in a propagation direction of the laser beam 20. Accordingly, the intensity of the laser beam 20 is increased. When the laser beam 20 is incident into the cone type hole 12, the intensity of the laser beam 20 may be increased by the cone type hole 12 or the cone type metal thin film, to thereby generate the ions 32 from the ion generation thin film 30. The ions 32 may be protons or carbon ions.

When the ions 32 are protons, the ion generation thin film 30 may be formed of a material containing hydrogen. The material containing hydrogen may be a silicon nitride, a silicon oxide, or a metal. When the ions 32 are carbon ions, the ion generation thin film 30 may include graphene, fullerenes in which carbon atoms are connected to one another in a spherical shape or a column shape, or carbon nanotube.

The cone type hole 12 of the substrate 10 may focus the laser beam 20 toward the ion generation thin film 30 to increase the intensity of the laser beam 20. A strengthen laser beam (see 21 of FIG. 2), formed by increasing the intensity of the laser beam 20 by the cone type hole 12, may transfer energy to the ion generation thin film 30. Thus, the ions 32 generated from the ion generation thin film 30 of the ion generation target may protons or carbon ions having a high energy level of tens to hundreds MeV. That is, the ions 32 generated from the ion generation thin film 30 of the ion generation target may have energy adjusted according to the shapes of the cone type holes 12. Thus, the ions 32 can be stopped at the tumor portion 54 in the patient, and collide with the tumor portion 54.

The ions 32 may be set to be projected onto a position of the tumor portion 180 obtained from image diagnosis devices such as a magnetic resonance imaging (MRI) device, a computer tomography (CT) device, a positron emission tomography (PET) device, and an ultrasonic wave device, which are used for diagnosing the tumor portion 54 of the patient.

According to a treatment principle of the ion beam treatment apparatus, the laser beam 20 emitted from the laser 40 may be introduced into the cone type hole 12 of the substrate 10 of the ion generation target, and be strengthened within the cone type hole 12 to generate the ions 32 from the ion generation thin film 30. Then, the ions 32 may be projected into the body of the patient and be stopped at the tumor portion 54 located inside of the body of the patient according to a Bragg peak principle. At this point, the ions 32 may collide with the tumor portion 54 to generate free oxygen radicals, thereby disturbing tumor cells of the tumor portion 54.

That is, since the ions 32 collide with the tumor portion 54 to generate the free oxygen radicals, thereby disturbing the tumor cells of the tumor portion 54, the growth of the tumor cells may be thwarted or the tumor cells may be necrotized. Here, the disturbance of the tumor cells of the tumor portion 54 by the ions 32 may represent disturbance of DNA double helices of the tumor cells or disturbance of metabolic processes within nuclei of the tumor cells.

According to the generation and projection processes of the ions 32, when the laser beam 20 is incident into the cone type hole 12 of the substrate 10 of the ion generation target and is strengthened within the cone type hole 12, hydrogen atoms or carbon ions contained in the ion generation thin film 30 are changed to a plasma state in which the hydrogen atoms or carbon ions are divided into positive ions 32 and negative ions (not shown) by the energy of the strengthened laser beam 20. In this process, the negative ions further move away from the ion generation thin film 30 than the positive ions 32 to generate an electric field by a capacitor effect between the positive ions 32 and the negative ions. The positive ions 32 are accelerated toward the negative ions by the electric field so that each of the positive ions 32 has energy enough to be projected onto the tumor portion 54 located inside of the body of the patient from the outside of the body.

Since the accelerated positive ions 32 collide with the tumor portion 54 to generate the free oxygen radicals, thereby disturbing the tumor cells of the tumor portion 54, the growth of the tumor cells may be thwarted or the tumor cells may be necrotized. Therefore, the tumor portion 54 within the body of the patient may be treated.

According to the embodiments, since an ion generation target has a cone type hole, the intensity of a laser beam incident into the ion generation target can be increased. Thus, the ion generation target can generate protons or carbon ions of high energy without increasing the power of a laser.

In addition, since an ion beam treatment apparatus uses the ion generation target having the cone type hole, protons or carbon ions of high energy can be projected onto a tumor portion in a patient. Thus, the ion beam treatment apparatus is adapted to economically treat a tumor portion in a patient.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An ion generation target comprising:
    a substrate including a first surface and a second surface opposed to the first surface and a cone type hole, the cone type hole having a top surface and a bottom surface in the first surface and the second surface of the substrate, respectively, the cone type hole penetrating through the substrate such that a cross-sectional area of the cone type hole continuously decreases from the top surface to the bottom surface, the cross-sectional area parallel to the top and bottom surfaces of the cone type hole, the cone type hole further having a sidewall surface that has a reflectivity higher than that of the substrate; and
    an ion generation thin film attached to the second surface of the substrate such that a portion of the ion generation thin film contacts the bottom surface of the cone type hole, the ion generation thin film configured to generate ions when a laser beam incident through the top surface of the cone type hole strikes the contacting portion of the ion generation thin film, an intensity of the laser beam increasing when the laser beam penetrates through the cone type hole from the top surface to the bottom surface.

2. The ion generation target of claim 1, wherein the substrate comprises a metal material.

3. The ion generation target of claim 2, wherein the metal material comprises silver, copper, gold, or aluminum.

4. The ion generation target of claim 1, wherein the substrate comprises an insulating material.

5. The ion generation target of claim 4, further comprising a cone type metal thin film on the sidewall surface of the cone type hole.

6. The ion generation target of claim 5, wherein the cone type metal thin film comprises silver, copper, gold, or aluminum.

7. The ion generation target of claim 5, wherein an inner circumferential surface of the cone type metal thin film is treated by mirror-like finishing.

8. The ion generation target of claim 1, wherein the sidewall surface of the cone type hole is treated by mirror-like finishing.

9. The ion generation target of claim 1, further comprising inert gas in the cone type hole.

10. The ion generation target of claim 1, wherein the cone type hole has a diameter on the order of 10 μm in the first surface of the substrate, and a diameter ranging between on the order of 10 nm and on the order of 1 μm in the second surface of the substrate.

11. The ion generation target of claim 1, wherein the ions are protons or carbon ions.

12. The ion generation target of claim 11, wherein the ions are protons, and the ion generation thin film is formed of a material containing hydrogen.

13. The ion generation target of claim 12, wherein the material containing hydrogen is a silicon nitride, a silicon oxide, or a metal.

14. The ion generation target of claim 11, wherein the ions are carbon ions, and the ion generation thin film comprises graphene, fullerenes in which carbon atoms are connected to one another in a spherical shape or a column shape, or carbon nanotube.

15. The ion generation target of claim 1, wherein the substrate comprises cone type holes that are distributed in a predetermined arrangement.

16. An ion beam treatment apparatus comprising:
    an ion generation target comprising:
        a substrate including a first surface and a second surface opposed to the first surface and a cone type hole, the cone type hole having a top surface and a bottom surface in the first surface and the second surface of the substrate, respectively, the cone type hole penetrating through the substrate such that a cross-sectional area of the cone type hole continuously decreases from the top surface to the bottom surface, the cross-sectional area parallel to the top and bottom surfaces of the cone type hole, the cone type hole further having a sidewall surface that has a reflectivity higher than that of the substrate; and
        an ion generation thin film attached to the second surface of the substrate such that a portion of the ion generation thin film contacts the bottom surface of the cone type hole, the ion generation thin film configured to generate ions when a laser beam incident through the top surface of the cone type hole strikes the contacting portion of the ion generation thin film, an intensity of the laser beam increasing when the laser beam penetrates through the cone type hole from the top surface to the bottom surface; and
    a laser that emits thee laser beam into the top surface of the cone type hole project the generated ions onto a tumor portion of a patient.

17. The ion beam treatment apparatus of claim 16, wherein the sidewall surface of the cone type hole is treated by mirror-like finishing.

18. The ion beam treatment apparatus of claim 16, further comprising inert gas in the cone type hole.

19. The ion beam treatment apparatus of claim 16, wherein the laser is disposed at a side of the first surface of the substrate.

20. The ion beam treatment apparatus of claim 16, wherein the laser beam is a femtosecond laser beam.

* * * * *